United States Patent [19]
Napolitano et al.

[11] Patent Number: 5,651,368
[45] Date of Patent: Jul. 29, 1997

[54] BLOOD PRESSURE CUFF COVER

[76] Inventors: John M. Napolitano, 1 Teresa Ct., Moonachie, N.J. 07074; Harry B. Baker, III, 251 Innes Rd., Wood-Ridge, N.J. 07075

[21] Appl. No.: 499,937

[22] Filed: Jul. 10, 1995

[51] Int. Cl.$^6$ .................................................. A61B 5/02
[52] U.S. Cl. .......................... 128/677; 128/672; 128/680; 128/681; 128/687
[58] Field of Search .................... 128/672, 677–686, 128/687, 853, 856; 606/202, 203; 224/901, 901.2, 901.4, 901.5, 901.8; 206/303, 363

[56] References Cited

U.S. PATENT DOCUMENTS

| | | | |
|---|---|---|---|
| 4,244,499 | 1/1981 | Adams | 224/901.8 |
| 4,548,249 | 10/1985 | Slaughterbeck | 128/686 |
| 4,967,758 | 11/1990 | Masciarotte | 128/686 |
| 4,979,613 | 12/1990 | McLaughlin et al. | 224/901 |
| 5,228,448 | 7/1993 | Byrd | 128/686 |

*Primary Examiner*—Lee S. Cohen
*Assistant Examiner*—Bryan K. Yarnell

[57] ABSTRACT

A cover for enclosing a blood pressure cuff. The inventive device includes a cuff envelope for receiving the blood pressure cuff. A window panel extends through the cuff envelope for permitting viewing of a gauge of the cuff therethrough. A conduit envelope extends from the cuff envelope and terminates in a bulb envelope for receiving the conduit and bulb extending from the cuff. Hook and loop fasteners are coupled to the cuff envelope for permitting securement of the protected blood pressure cuff about a limb of an individual.

1 Claim, 3 Drawing Sheets

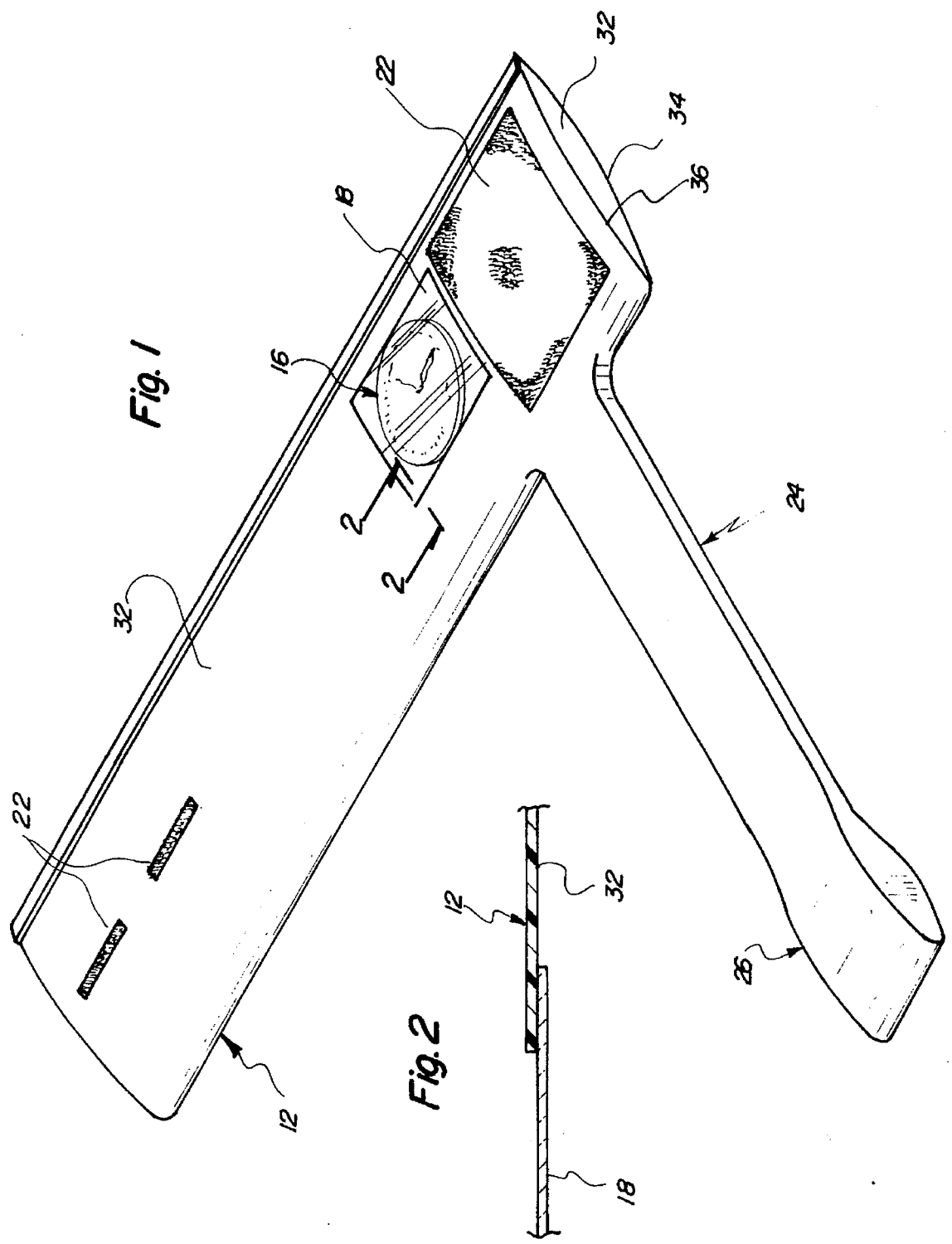

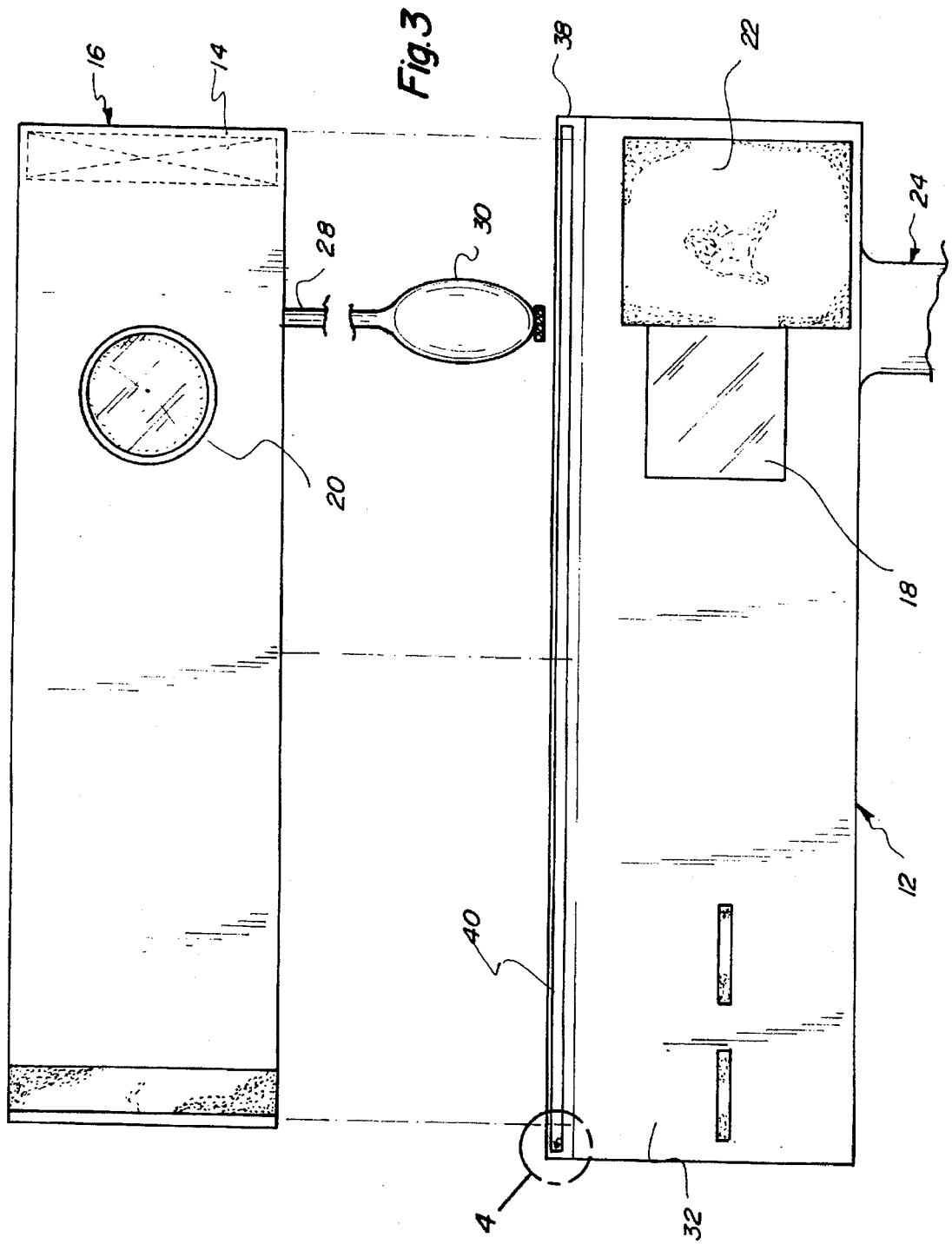

BLOOD PRESSURE CUFF COVER

BACKGROUND OF THE INVENTION

1. Field of the Invention

The present invention relates to medical devices and more particularly pertains to a blood pressure cuff cover for enclosing a blood pressure cuff.

2. Description of the Prior Art

The use of medical devices is known in the prior art. More specifically, medical devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art medical devices include U.S. Pat. No. 3,760,795; U.S. Pat. No. 3,773,036; U.S. Pat. No. 4,548,249; U.S. Pat. No. 4,967,758; U.S. Pat. No. 5,201,758; and U.S. Pat. No. 5,228,448.

While these devices fulfill their respective, particular objectives and requirements, the aforementioned patents do not disclose a blood pressure cuff cover for enclosing a blood pressure cuff which includes a cuff envelope for receiving the blood pressure cuff, a window panel extending through the cuff envelope for permitting viewing of a gauge of the cuff therethrough, a conduit envelope extending from the cuff envelope and terminating in a bulb envelope for receiving the conduit and bulb extending from the cuff, and hook and loop fasteners coupled to the cuff envelope for permitting securement of the protected blood pressure cuff about a limb of an individual.

In these respects, the blood pressure cuff cover according to the present invention substantially departs from the conventional concepts and designs of the prior art, and in so doing provides an apparatus primarily developed for the purpose of enclosing a blood pressure cuff to protect the same from contact with hazardous fluids.

SUMMARY OF THE INVENTION

In view of the foregoing disadvantages inherent in the known types of medical devices now present in the prior art, the present invention provides a new blood pressure cuff cover construction wherein the same can be utilized for protecting a blood pressure cuff. As such, the general purpose of the present invention, which will be described subsequently in greater detail, is to provide a new blood pressure cuff cover apparatus and method which has many of the advantages of the medical devices mentioned heretofore and many novel features that result in a blood pressure cuff cover which is not anticipated, rendered obvious, suggested, or even implied by any of the prior art medical devices, either alone or in any combination thereof.

To attain this, the present invention generally comprises a cover for enclosing a blood pressure cuff. The inventive device includes a cuff envelope for receiving the blood pressure cuff. A window panel extends through the cuff envelope for permitting viewing of a gauge of the cuff therethrough. A conduit envelope extends from the cuff envelope and terminates in a bulb envelope for receiving the conduit and bulb extending from the cuff. Hook and loop fasteners are coupled to the cuff envelope for permitting securement of the protected blood pressure cuff about a limb of an individual.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new blood pressure cuff cover apparatus and method which has many of the advantages of the medical devices mentioned heretofore and many novel features that result in a blood pressure cuff cover which is not anticipated, rendered obvious, suggested, or even implied by any of the prior art medical devices, either alone or in any combination thereof.

It is another object of the present invention to provide a new blood pressure cuff cover which may be easily and efficiently manufactured and marketed.

It is a further object of the present invention to provide a new blood pressure cuff cover which is of a durable and reliable construction.

An even further object of the present invention is to provide a new blood pressure cuff cover which is susceptible of a low cost of manufacture with regard to both materials and labor, and which accordingly is then susceptible of low prices of sale to the consuming public, thereby making such blood pressure cuff covers economically available to the buying public.

Still yet another object of the present invention is to provide a new blood pressure cuff cover which provides in the apparatuses and methods of the prior art some of the advantages thereof, while simultaneously overcoming some of the disadvantages normally associated therewith.

Still another object of the present invention is to provide a new blood pressure cuff cover for enclosing a blood pressure cuff to protect the same from contact with hazardous fluids.

Yet another object of the present invention is to provide a new blood pressure cuff cover which includes a cuff envelope for receiving the blood pressure cuff, a window panel extending through the cuff envelope for permitting viewing of a gauge of the cuff therethrough, a conduit envelope extending from the cuff envelope and terminating in a bulb envelope for receiving the conduit and bulb extending from the cuff, and hook and loop fasteners coupled to the cuff envelope for permitting securement of the protected blood pressure cuff about a limb of an individual.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a blood pressure cuff cover according to the present invention in use.

FIG. 2 is a cross sectional view taken along line 2—2 of FIG. 1.

FIG. 3 is an elevation view of the invention showing placement of a blood pressure device thereinto.

DESCRIPTION OF THE PREFERRED EMBODIMENT

Figure 4:
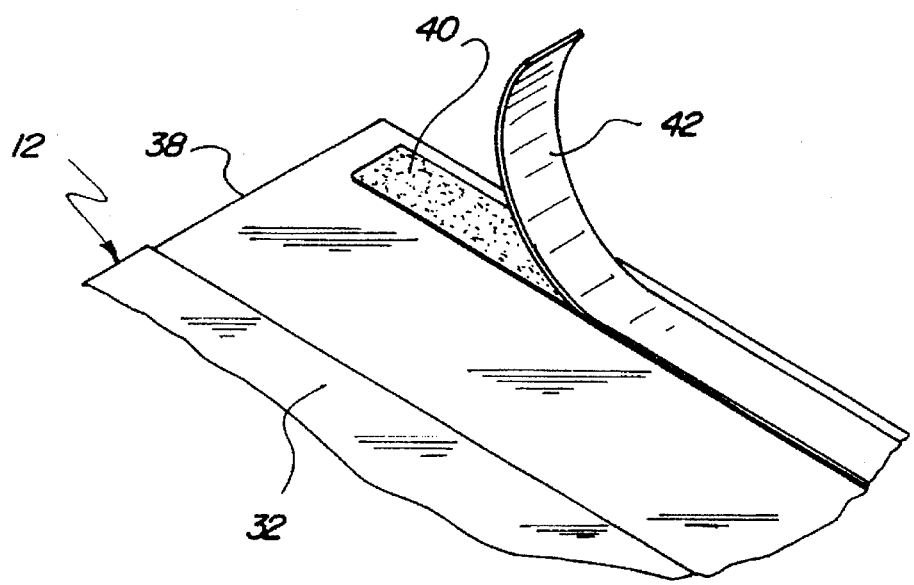
FIG. 4 is an enlarged isometric illustration of the area set forth in FIG. 3.

With reference now to the drawings, and in particular to FIGS. 1–5 thereof, a new blood pressure cuff cover embodying the principles and concepts of the present invention and generally designated by the reference numeral 10 will be described.

More specifically, it will be noted that the blood pressure cuff cover 10 comprises a cuff envelope 12 adapted to receive a cuff 14 of a blood pressure device 16, as shown in FIGS. 1 and 3 of the drawings. The cuff envelope 12 is shaped so as to define an unlabeled window aperture directed therethrough having a window panel 18 of transparent construction extending across the window aperture and permitting an individual to view a gauge 20 of the blood pressure device 16 therethrough. Hook and loop fasteners 22 are secured to various exterior portions of the cuff envelope 12 for permitting the device 10 having the blood pressure device 16 positioned therewithin to be wrapped about a limb of an individual to facilitate the ascertaining of blood pressure by a conventionally known procedure. By this structure, the cuff 14 of the blood pressure device 16 is substantially shielded from contact with hazardous fluids such as blood or the like.

With continuing reference to FIGS. 1 and 3, it can be shown that the present invention 10 may further comprise a conduit envelope 24 coupled to the cuff envelope 12 and extending therefrom to terminate in a bulb envelope 26. The conduit envelope 24 and the bulb envelope 26 are positioned in contiguous communication with an interior of the cuff envelope 12 so as to receive a pneumatic conduit 28 and a pneumatic bulb 30 of the blood pressure device 16. By this structure, the pneumatic conduit 28 and the pneumatic bulb 30 are similarly shielded form contact with hazardous fluids or the like. As can be seen in FIG. 1, the conduit envelope 24 must be of a transverse width or diameter sufficient to allow passage of the pneumatic bulb 30 therethrough for positioning of the bulb into the bulb envelope 26.

As best illustrated in FIGS. 1 through 4, it can be shown that the cuff envelope 12 of the present invention 10 preferably comprises a substantially rectangular outer web 32 coupled to and coextensively covering an inner web 34 of similar configuration relative to the outer web 32. Lateral or transverse edges of the inner and outer web 32 and 34 can be directly secured together. Alternatively, end webs 36 can extend between the transverse edges of the outer web 32 and the inner web 34 as shown in FIG. 1 of the drawings. The outer web 32 includes spaced and parallel longitudinal edges, with a lower longitudinal edge being coupled to a lower longitudinal edge of the inner web 34. The upper longitudinal edges of the outer web 32 and the inner web 34 are separated and permit insertion of the cuff 14 of the blood pressure device 16 into the cuff envelope 12 as shown in FIG. 3 of the drawings. To secure the blood pressure device 16 within the present invention 10, the inner web 34 is preferably shaped so as to define a securing flap 38 extending therefrom which can be folded on top of the outer web 32 and secured relative thereto. To this end, and as shown in FIGS. 3 and 4, an adhesive strip 40 extends along the securing flap 38 to permit adhesive securement thereof to the exterior surface of the outer web 32. The adhesive strip 40 is preferably initially covered by a removable backing 42 which can be selectively separated therefrom to expose the adhesive strip for securement to the outer web 32. By this structure, the cuff 14 can be securely held within the cuff envelope 12.

As shown in FIG. 2, the window panel 18 can be adhesively or otherwise mechanically secured by stitching or the like to the outer web 32 of the cuff envelope 12. The window panel 18 thus operates to permit viewing of the gauge 20 of the blood pressure device 16 therethrough during a blood pressure procedure.

Figure 5:
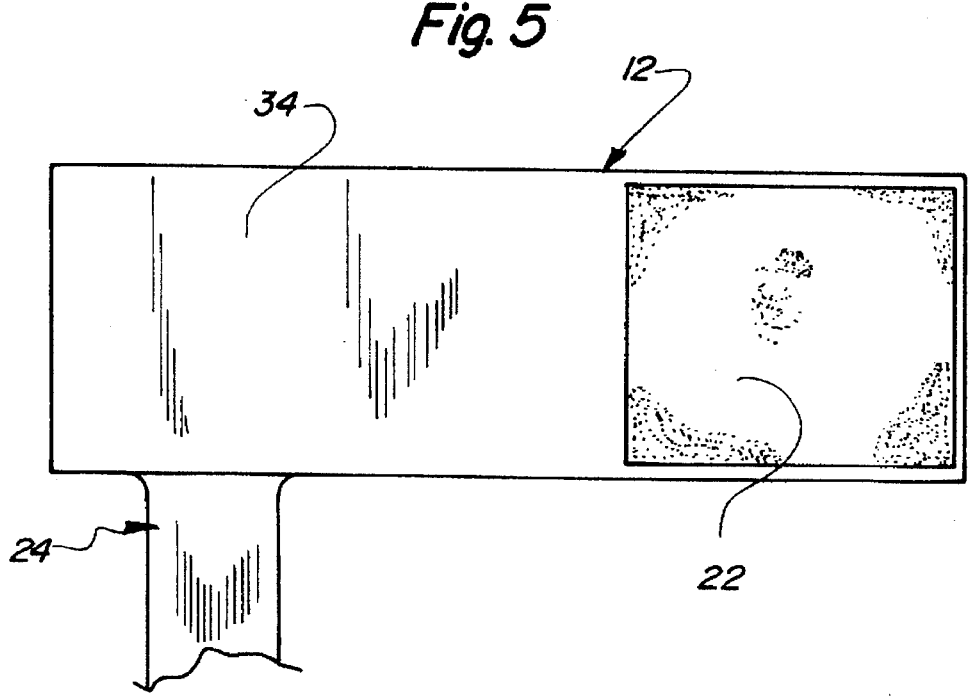
FIG. 5 is a rear elevation view of the invention.

As shown in FIG. 5, the hook and loop fasteners 22 are preferably secured to the outer web 32 and the inner web 34 of the cuff envelope 12 to permit circumferential wrapping and securing of the cuff envelope 12 about a limb of an individual prior to commencing of a blood pressure procedure.

In use, the blood pressure cuff cover 10 of the present invention can be easily utilized to protect a blood pressure device 16 from contact with contaminating or hazardous materials such as blood or the like. The present invention 10 can be entirely constructed of a substantially disposable material wherein the entire device may simply be discarded subsequent to being contaminated by a hazardous fluid or the like.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A blood pressure cuff cover comprising:

a cuff envelope adapted to removably receive a cuff of a blood pressure device, the cuff envelope being shaped so as to define a window aperture directed therethrough permitting an individual to view a gauge of the blood pressure device therethrough, the cuff envelope comprises a substantially rectangular outer web and a substantially rectangular inner web coupled to and coextensively covering the outer web, the outer web including spaced and parallel upper and lower longitudinal edges, and the inner web including spaced and parallel upper and lower longitudinal edges, with the lower longitudinal edge of the outer web being coupled to the lower longitudinal edge of the inner web, the upper longitudinal edges of the outer web and the inner web being separated to permit insertion of a cuff of a blood pressure device into the cuff envelope, one of the webs is shaped so as to define a securing flap extending therefrom which can be folded on top of another of the webs and secured relative thereto, an adhesive strip extending along the securing flap to permit adhesive securement thereof to an exterior surface of one of the webs;

a window panel of transparent construction extending across the window aperture;

hook and loop fasteners secured to exterior portions of the cuff envelope permitting securement of the cuff envelope about a limb of an individual;

a conduit envelope coupled to the cuff envelope and extending therefrom to terminate in a bulb envelope, the conduit envelope and the bulb envelope positioned in contiguous communication with an interior of the cuff envelope and being adapted to receive a pneumatic conduit and a pneumatic bulb of the blood pressure device, the conduit envelope is of a transverse width sufficient to allow passage of a pneumatic bulb therethrough for positioning of the bulb into the bulb envelope.

* * * * *